(12) United States Patent
Boulton et al.

(10) Patent No.: US 7,026,479 B2
(45) Date of Patent: Apr. 11, 2006

(54) PROCESS FOR THE PRODUCTION OF QUINAZOLINES

(76) Inventors: Lee Terence Boulton, c/o Pfizer Limited, United Kingdom Patent Department, Ramsgate Road, Sandwich Kent CT13 9NJ (GB); Robert James Crook, Pfizer Global Research and Development, Ramsgate Road, Sandwich, Kent CT13 9NJ (GB); Alan John Pettman, Pfizer Global Research and Development, Ramsgate Road, Sandwich, Kent CT13 9NJ (GB); Robert Walton, Pfizer Global Research and Development, Ramsgate Road, Sandwich, Kent CT13 9NJ (GB)

( * ) Notice: Subject to any disclaimer, the term of this patent is extended or adjusted under 35 U.S.C. 154(b) by 508 days.

(21) Appl. No.: 10/199,755

(22) Filed: Jul. 19, 2002

(65) Prior Publication Data

US 2003/0100753 A1 May 29, 2003

Related U.S. Application Data

(60) Provisional application No. 60/328,369, filed on Oct. 9, 2001.

(30) Foreign Application Priority Data

Aug. 1, 2001 (GB) .................... 0118752

(51) Int. Cl.
*C07D 239/70* (2006.01)
*C07D 237/02* (2006.01)

(52) U.S. Cl. .............. 544/253; 544/224; 544/242
(58) Field of Classification Search ............ 544/253, 544/224, 242
See application file for complete search history.

(56) References Cited

FOREIGN PATENT DOCUMENTS

WO        WO98/30562      *  7/1998

OTHER PUBLICATIONS

Seijas et al., "Microwave enhanced synthesis of 4-aminoquinazolines", Tetrahedron Letters 41, (2000) 2215-2217.*
Seijas, J. A., et al., Tetrahedron Letters, vol. 41, pp. 2215-2217, 2000, "Microwave Enhanced Synthesis of 4-Aminoquinazolines".
Bailey, D. M., et al., Journal of Medicinal Chemistry, vol. 16, No. 2, pp. 151-156, 1973, "Hydroxyguanidines. A New Class of Antihypertensive Agents".

* cited by examiner

*Primary Examiner*—James O. Wilson
*Assistant Examiner*—Paul V. Ward
(74) *Attorney, Agent, or Firm*—Gregg C. Benson; Carl J. Goddard

(57) ABSTRACT

The invention provides a process for the production of a compound of formula (A), or a pharmaceutically acceptable salt or solvate thereof,

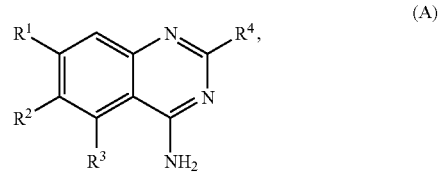

(A)

wherein $R^1$, $R^2$, $R^3$, and $R^4$ are as defined herein.

32 Claims, No Drawings

PROCESS FOR THE PRODUCTION OF QUINAZOLINES

This application is filed claiming priority from now abandoned U.S. Provisional Application Ser. No. 60/328,369, filed on Oct. 9, 2001 and GB Provisional Application Ser. No. 0118752.5, filed on Aug. 1, 2001.

This invention relates to a novel process for producing quinazoline compounds which are useful in therapy. More specifically, the compounds are useful in the treatment of benign prostatic hyperplasia.

International Patent Application WO 98/30560 discloses a number of substituted quinoline and quinazoline compounds of formula (I) which find use in the treatment of benign prostatic hyperplasia,

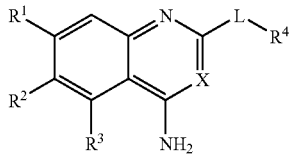

wherein
$R^1$ represents $C_{1-4}$ alkoxy optionally substituted by one or more fluorine atoms;
$R^2$ represents H or $C_{1-6}$ alkoxy optionally substituted by one or more fluorine atoms;
$R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
$R^4$ represents a 4-, 5-, 6-, or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^8R^9$, $SO_2NR^8R^9$, $(CH_2)_bNR^8R^9$ and $NHSO_2(C_{1-4}$ alkyl), and when S is a member of the ring system, it may be substituted by one or two oxygen atoms;
$R^8$ and $R^9$ independently represent H or $C_{1-4}$ alkyl, or together with the N atom to which they are attached they may represent a 5- or 6-membered heterocyclic ring containing at least one heteroatom selected from N, O and S;
b represents 0, 1, 2 or 3;
X represents CH or N; and
L is absent,
or represents a cyclic group of formula Ia,

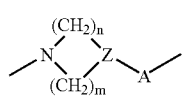

in which N is attached to the 2-position of the quinoline or quinazoline ring;
A is absent or represents CO or $SO_2$;
Z represents CH or N;
m represents 1 or 2, and in addition, when Z represents CH, it may represent 0; and
n represents 1, 2 or 3, provided that the sum of m and n is 2, 3, 4 or 5;
or represents a chain of formula Ib,

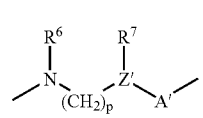

in which N is attached to the 2-position of the quinoline or quinazoline ring;
A' and Z' have the same significance as A and Z above, respectively;
$R^6$ and $R^7$ independently represent H or $C_{1-4}$ alkyl; and
p represents 1, 2 or 3, and in addition, when Z' represents CH, it may represent 0.

The compounds of formula (I) in which X represents N, and L is absent are of particular interest. Of these compounds, 4-amino-2-(5-methanesulfonamido-1,2,3,4-tetrahydro-2-isoquinolyl)-6,7-dimethoxy-5-(2-pyridyl)quinazoline is of special interest.

According to WO 98/30560, the compounds of formula (I) can be produced by a number of processes. However, none of these processes involves the condensation of the two main parts of the molecule in a convergent synthesis in which the quinazoline ring is formed and each process suffers disadvantages. For example, 4-amino-2-(5-methanesulfonamido-1,2,3,4-tetrahydroisoquinol-2-yl)-6,7-dimethoxy-5-(2-pyridyl)quinazoline (the compound of Example 19 in WO 98/30560) is prepared according to the following scheme:

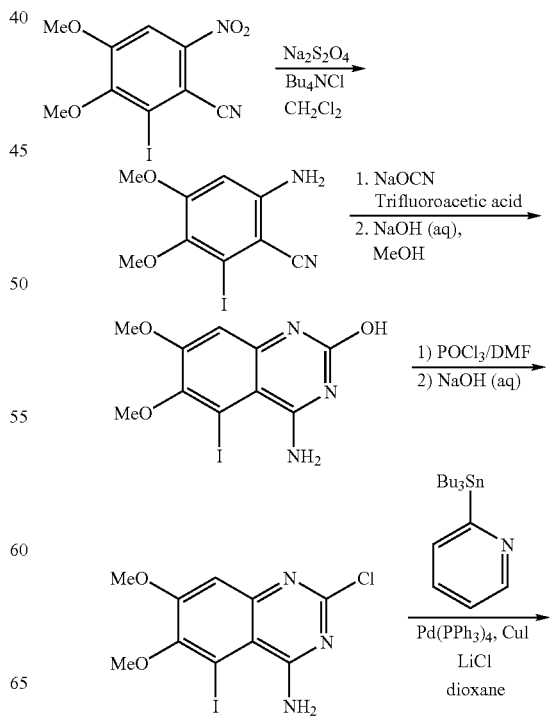

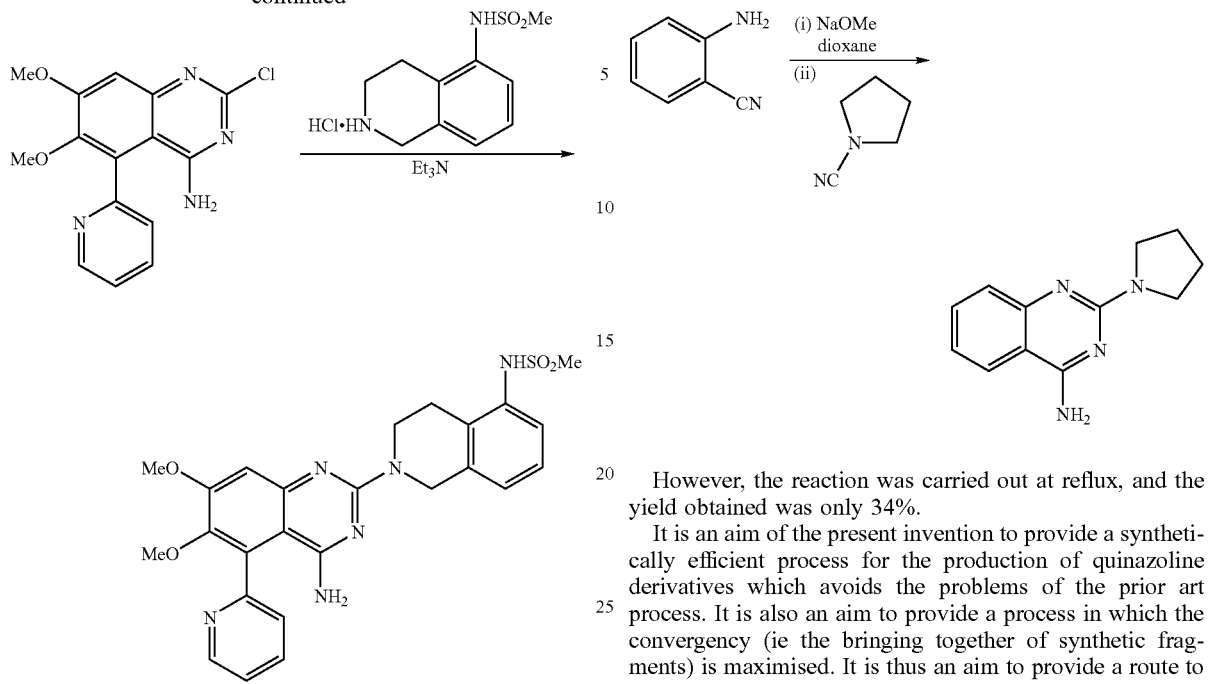

The routes described in WO 98/30560 suffer the disadvantage that they involve the use of tributyl stannyl pyridine in combination with copper iodide and tetrakis (triphenylphosphine) palladium. One problem of this route is that the tributyl stannyl pyridine is expensive to purchase. The compound is toxic and there are issues of worker safety and concerning the environment. After use, spent reactants are difficult and expensive to dispose of because of the adverse effects organotin compounds have on their surroundings. A further problem with the prior art process is its lack of convergency. A number of synthetic steps are required to produce the quinazoline compounds in the disclosed processes, with each synthetic step leading both to a reduction in yield and increasing the possibility of competing side reactions. Thus the conventional sequence requires effort to purify the product and may not give an optimal yield.

A further problem with the prior art process of WO 98/30560 is that large pebble-like aggregates are formed in the reactor during the reaction. The identity of these aggregates is not clear but they are believed to be formed of inorganic material derived from the various inorganic additives used during the reaction such as lithium chloride and copper iodide. In this process, there is the risk that the pebble-like aggregates could crack the reactor causing leakage of the reaction medium and the hazard of fire or poisoning. At the very least there is the problem that the reaction leads to scratching of the interior of the reaction vessel thus causing premature wearing of the vessel, poor heat dissipation in the mixture or blocking.

The use of sodium methoxide in dioxane has been reported recently for the synthesis of 2-aminoquinazolines (see van Muijlwijk-Koezen et al, J Med Chem, 2000, vol 43 (11), p2227–2238, in particular the preparation of compound 4k):

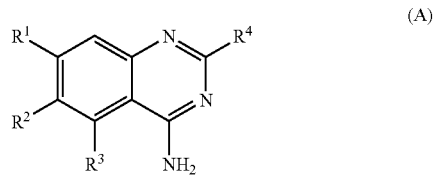

However, the reaction was carried out at reflux, and the yield obtained was only 34%.

It is an aim of the present invention to provide a synthetically efficient process for the production of quinazoline derivatives which avoids the problems of the prior art process. It is also an aim to provide a process in which the convergency (ie the bringing together of synthetic fragments) is maximised. It is thus an aim to provide a route to the compounds of formula (I) of greatest interest which offers an improved yield relative to the existing routes. It is a further aim of the process of the present invention to avoid the use of organotin compounds on account of their hazardous nature. It is a further aim of the present invention to provide a process which minimizes the number of synthetic steps required and which avoids the problem of competing reactions and/or the disposal of hazardous materials. It is also desirable to avoid heating of reaction mixtures where possible.

We have found an improved route to the quinazoline derivatives of formula (I) above of greatest interest which satisfies some or all of the above aims.

According to the present invention, there is provided a process for the production of a compound of formula (A), or a pharmaceutically acceptable salt or solvate thereof, (A)

wherein
$R^1$ represents $C_{1-4}$ alkoxy optionally substituted by one or more fluorine atoms;
$R^2$ represents H or $C_{1-6}$ alkoxy optionally substituted by one or more fluorine atoms;
$R^3$ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
$R^4$ is a 4-, 5-, 6- or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^7R^8$, $SO_2NR^7R^8$, $(CH_2)_bNR^7R^8$ and $NHSO_2(C_{1-4}$ alkyl), and when S is a member of the ring system, it may be substituted by 1 or 2 oxygen atoms;

$R^7$ and $R^8$ independently represent H or $C_{1-4}$ alkyl, or together with the N atom to which they are attached they may represent a 5- or 6-membered heterocyclic ring containing at least one heteroatom selected from N, O and S; and b represents 0, 1, 2 or 3;

the process comprising condensing a compound of formula (B),

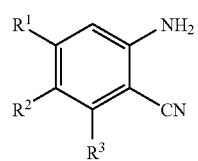

wherein
$R^1$ to $R^3$ are as defined above;

with a compound of formula (C),

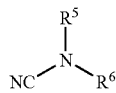

wherein
$R^5$ and $R^6$ taken together with the N atom to which they are attached represent a 4-, 5-, 6-, or 7-membered N-containing heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^7R^8$, $SO_2NR^7R^8$, $(CH_2)_bNR^7R^8$ and $NHSO_2(C_{1-4}$ alkyl), and when S is a member of the ring system, it may be substituted by 1 or 2 oxygen atoms;

$R^7$, $R^8$ and b are as defined above; and where necessary or desired, converting the resulting compound of formula (A) into a pharmaceutically acceptable salt or solvate, or converting the resulting salt or solvate into a compound of formula (A).

Preferably $R^1$ represents methoxy.
Preferably $R^2$ represents methoxy.
Preferably $R^3$ represents an aromatic ring. More preferably, $R^3$ represents pyridyl, pyrimidyl, thienyl, furanyl or oxazolyl. More preferably $R^3$ represents 2-pyridyl or 2-pyrimidyl, 2-pyridyl being most preferred.

Preferably, $R^5$ and $R^6$ together with the N atom to which they are attached represent a saturated 6-membered N-containing ring which is fused to an optionally substituted benzene or pyridine ring. More preferably, $R^5$ and $R^6$ together with the N atom to which they are attached represent an optionally substituted tetrahydroisoquinoline ring system. Most preferably, $R^5$ and $R^6$ together with the N atom to which they are attached represent a group of formula

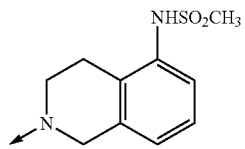

Thus, the process is most preferably used to prepare 4-amino-2-(5-methanesulfonamido-1,2,3,4-tetrahydro-2-isoquinolyl)-6,7-dimethoxy-5-(2-pyridyl)quinazoline.

Preferably the reaction is carried out in a polar aprotic solvent, for example dimethylsulfoxide.

Preferably, the reaction is carried out at a temperature in the range 10–30° C.

Preferably the reaction is carried out in the presence of a base. More preferably, the base is an alkali metal alkoxide or an alkaline earth metal alkoxide. More preferably, the base is sodium t-butoxide or sodium t-pentoxide, the latter being most preferred.

In a further aspect of the present invention, there is provided a process for the production of a compound of formula (C), as defined above, which comprises reaction of a compound of formula (E), $$HNR^5R^6 \qquad (E)$$

or an acid addition salt thereof, wherein $R^5$ and $R^6$ are as defined above, with BrCN in the presence of an amine base.

Preferably, the base is a tri-$C_{1-8}$ alkyl, $C_{3-8}$ cycloalkyl or a heterocyclic amine. Most preferably the base is N,N-diisopropylethylamine.

The invention also provides an alternative process for the production of a compound of formula (C), as defined above, which comprises reaction of a compound of formula (F),

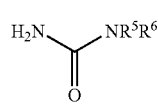

wherein $R^5$ and $R^6$ are as defined in claim 1, with methanesulphonyl chloride in the presence of pyridine. Compounds of formula (F) may be prepared from compounds of formula (E) by reaction with sodium cyanate in water, as illustrated by Example 3A(a). Compounds of formula (E) are either known or may be prepared by known techniques.

Preferably, the above two processes for preparing compounds of formula (C) are used to prepare N-(2-cyano-1,2,3,4-tetrahydro-5-isoquinolyl)methanesulfonamide.

In another aspect of the invention, there is provided a process for the production of a compound of formula (B),

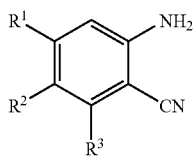

(B)

wherein
R[1] to R[3] are as defined above;
which comprises reaction of a compound of formula (D),

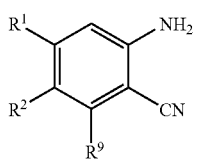

(D)

wherein;
R[1] and R[2] are as defined above; and
R[9] is a leaving group;
with a pyridyl boronate.

Preferably R[9] is iodine.

Preferably the pyridine derivative is a 2-pyridyl boronate.

Most preferably, the process is used to prepare 6-amino-3,4-dimethoxy-2-(2-pyridyl)benzonitrile.

Preferably, the reaction is carried out in a polar aprotic solvent. More preferably, the polar aprotic solvent is tetrahydrofuran or isopropyl acetate.

Preferably, the coupling reaction to form the 6-amino-3,4-dimethoxy-2-(2-pyridyl)benzonitrile is carried out above room temperature. Preferably, this reaction is carried out in the presence of a catalyst. More preferably, the catalyst is a palladium (0) catalyst. Most preferably, the catalyst is derived from palladium (II) acetate by reduction in situ. Preferably, this coupling reaction is carried out in the presence of a base. The base is preferably an alkali metal carbonate, and more preferably it is potassium carbonate.

The pyridyl boronate may be prepared by reaction of a bromopyridine with triisopropylborate at or below room temperature. Preferably, this reaction is carried out in the presence of a base. The base is preferably an alkyl lithium reagent. n-Butyl lithium is a preferred alkyl lithium reagent.

Compounds of formula (D) may be prepared from known compounds, or compounds that are readily prepared, using known techniques, as illustrated by Example 1.

The invention further provides compounds of formula (B), as defined above, and compounds of formula (C), as defined above.

The invention is illustrated by the following examples in which the following abbreviations may be used:

| | |
|---|---|
| DMSO = | dimethylsulfoxide |
| DCM = | dichloromethane |
| Et = | ethyl |
| EtOAc = | ethyl acetate |
| K$_2$EDTA = | ethylenediaminetetraacetic acid, dipotassium salt |
| nBuLi = | n-butyllithium |
| OAc = | acetate |
| THF = | tetrahydrofuran |

EXAMPLE 1

Preparation of
6-amino-2-iodo-3,4-dimethoxybenzonitrile

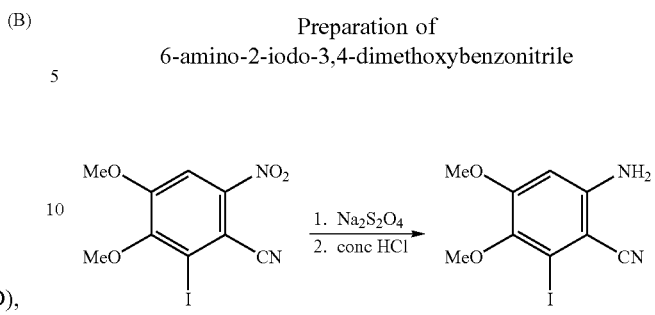

In a reactor vessel, a suspension of 6-nitro-2-iodo-3,4-dimethoxybenzonitrile (see Example 1(d) of WO 98/30560, 10 kg) in ethanol (60 l) at room temperature was charged with a solution of sodium dithionite (15.6 kg of technical grade material) in water (67.5 l) over 45 mins maintaining the temperature below 35° C. The addition vessel was washed with water (10 l). The resulting mixture was warmed to reflux (ca. 85° C.) for ca. 90 mins and then the temperature adjusted to 65° C. A solution of 6M aqueous hydrochloric acid (12.5 l) was added over ca. 10 mins and the resulting mixture stirred at 65° C. for ca. 5 hours before being cooled to room temperature. The pH was adjusted to the range 7–8 using 40% sodium hydroxide (2 l), the resulting mixture left to stir for 3 hours, filtered and washed with water (50 l). The damp cake was slurried in water (90 l) overnight at room temperature, filtered, washed with water (100 l) and dried in vacuo to give 8.35 kg (92%) of the title compound.

EXAMPLE 2

Preparation of
6-amino-3,4-dimethoxy-2-(2-pyridyl)benzonitrile (a) Preparation of the 2-pyridyl Boronate

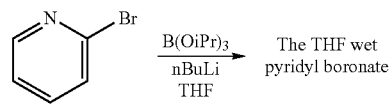

Under nitrogen, a stirred solution of 2-bromopyridine (150 g, 0.95 mol) and triisopropylborate (218 ml, 0.95 mol) in THF was cooled to −25° C. A 2.5M solution of n-BuLi in hexanes (378 ml, 0.95 mol) was added at such a rate that the temperature did not exceed −24° C. After completion of the addition, the reaction was allowed to warm to room temperature and stirred at this temperature for 18 hours. After this time, the reaction mixture was filtered, washed with THF and the procedure deemed complete before the filter pad had completely dried. A portion of the THF wet boronate was used in the subsequent reaction. Analysis of the THF wet boronate by $^1$H NMR, showed a pyridine H̲:isopropyl methine H̲ ratio of 1:3.75 and that the material contained 54% w/w solvent.

(b) Preparation of 6-amino-3,4-dimethoxy-2-(2-pyridyl)benzonitrile

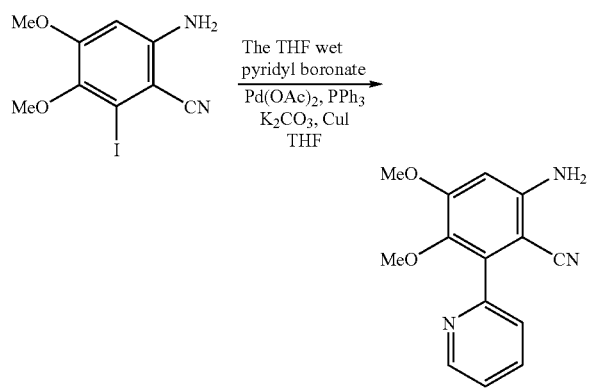

Under nitrogen, to anhydrous THF (1000 ml) was added 6-amino-2-iodo-3,4-dimethoxybenzonitrile (see Example 1, 50.0 g, 164 mmol), Pd(OAc)$_2$ (1.85 g, 8.22 mmol), PPh$_3$ (triphenylphosphine, 4.31 g, 16.4 mmol), THF wet boronate [from step (a), 286 g, 493 mmol], CuI (12.5 g, 65 mmol) and K$_2$CO$_3$ (45.5 g, 328 mmol). The reaction mixture was then stirred at reflux for 16 hours. After this time, the reaction mixture was cooled to room temperature and water (1000 ml) added. The mixture was then filtered through an Arbocel™ filter aid pad and the pad washed with THF (500 ml). The filtrate was then extracted with CH$_2$Cl$_2$ (1000 ml). The aqueous phase was back extracted with CH$_2$Cl$_2$ (500 ml) and the combined CH$_2$Cl$_2$ extracts were evaporated in vacuo to yield the crude product as a dark brown solid. Recrystallisation from EtOAc (250 ml) afforded 37.6 g (87%) of the title compound as a beige solid.

EXAMPLE 2A

Alternative Route to 6-amino-3,4-dimethoxy-2-(2-pyridyl)benzonitrile (a) Preparation of the N-phenyldiethanolamine Pyridyl Boronate

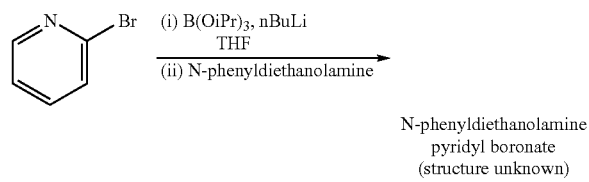

Under nitrogen, a stirred solution of 2-bromopyridine (843 g, 5.33 mol) and triisopropylborate (1.20 kg, 6.40 mol) in THF (6.74 l) was cooled to −75° C. A 1.6M solution of n-BuLi in hexanes (4.00 l, 6.40 mol) was added at such a rate that the temperature did not exceed −67° C. After completion of the addition, the reaction was allowed to warm to room temperature and stirred at this temperature for 16 hours. After this time, a solution of N-phenyldiethanolamine (966 g, 5.33 mol) in THF (966 ml) was added and the resulting mixture heated at reflux for 4 hours. The solvent was distilled and replaced with isopropanol until the head temperature was 76° C. (distilling 11.3 l and adding in 8.4 l of isopropanol during the process). The mixture was cooled to room temperature and stirred at this temperature for 12 hours. The mixture was filtered, the solid washed with isopropanol (1.7 l) and dried in vacuo overnight at 40° C. to give 1605 g of the subtitle compound. Analysis by $^1$H NMR showed a ratio of pyridine: N-phenyldiethanolamine (or lithium alkoxide): isopropyl of 1:1.25:1.55.

(b) Preparation of 6-amino-3,4-dimethoxy-2-(2-pyridyl)benzonitrile

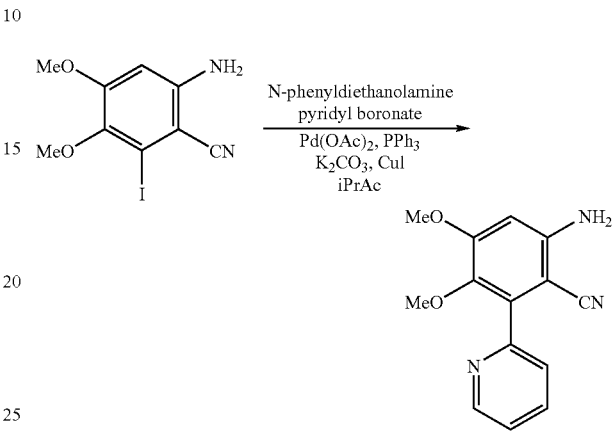

Under nitrogen, 6-amino-2-iodo-3,4-dimethoxybenzonitrile (see Example 1, 100 g, 0.33 mol) was suspended in isopropyl acetate (1.4 L) at 20° C. To the suspension was charged palladium acetate (3.69 g, 16 mmol), followed by triphenylphosphine (17.25 g, 66 mmol), N-phenyldiethanolamine pyridyl boronate (263.4 g of the batch prepared as described above), copper iodide (25.05 g, 0.13 mol), then potassium carbonate (90.9 g, 0.66 mol) and the suspension heated to reflux for 8 hours. The suspension was cooled to 70° C. and maintained at this temperature overnight. The suspension was cooled to 45° C., tetrahydrofuran (1 l) was added and the suspension stirred at 45° C. for 1 hour. After this time, Arbocel™ filter aid was added and the mixture was filtered through Arbocel™ filter aid. The pad was washed with tetrahydrofuran (2×200 ml) and isopropyl acetate (200 ml). The resulting solution was washed twice with a 1:1 mixture of 5% aqueous K$_2$EDTA and saturated brine (800 ml), then washed with a 1:1 mixture of water and saturated brine (800 ml). The organic phase was distilled and replaced with isopropyl acetate to leave a final volume of isopropyl acetate of 500 ml that was left to cool to room temperature overnight. The resulting suspension was filtered to give a light brown solid that was dried in vacuo overnight at 45° C. to yield 59.6 g (71%) of the title compound.

EXAMPLE 3

Preparation of N-(2-cyano-1,2,3,4-tetrahydro-5-isoquinolyl)methanesulfonamide

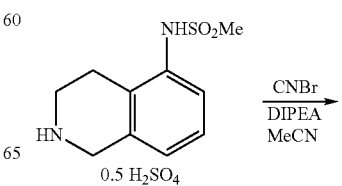

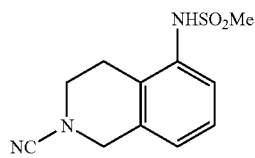

To a stirred slurry of N-(1,2,3,4-tetrahydro-5-isoquinolyl)methanesulfonamide hemisulfate (prepared analogously to the compound of Example 19(b) in WO 98/30560, but using sulphuric acid in the final step in place of hydrochloric acid; 240 g, 0.88 mol) in acetonitrile (2400 ml) at 0° C. was added N,N-diisopropylethylamine (326 ml, 1.88 mmol). Cyanogen bromide (99.2 g, 0.94 mol) was added over a period of 20 minutes keeping the temperature below 10° C. The resulting slurry was allowed to warm to 20° C. and stirred at this temperature for 18 hrs. After this time, water (2400 ml) was added and the resulting mixture extracted with $CH_2Cl_2$ (2×2500 ml). The combined organic phases were washed with water (2000 ml) and evaporated to dryness. The resulting solid was reslurried in $CH_2Cl_2$ (360 ml) and the solid collected by filtration to yield 158 g (72%) of the title compound.

EXAMPLE 3A

Alternative Route to N-(2-cyano-1,2,3,4-tetrahydro-5-isoquinolyl)methane-sulfonamide (a) Preparation of N-(2-carboxamide-1,2,3,4-tetrahydro-5-isoguinolyl)methane-sulfonamide

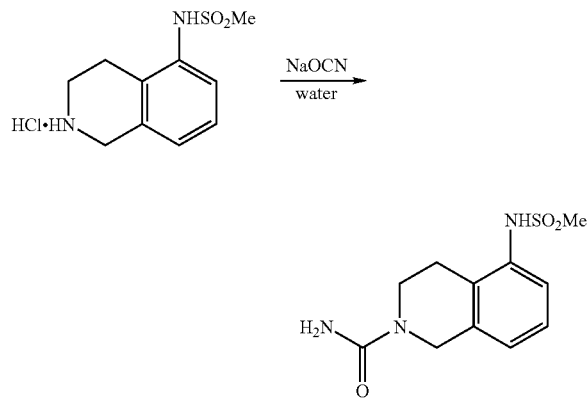

Under nitrogen, N-(1,2,3,4-tetrahydro-5-isoquinolyl)methanesulfonamide hydrochloride (see Example 19(b), WO 98/30560, 50 g, 190 mmol) was suspended in water (250 ml) at 20° C. A solution of sodium cyanate (16.1 g, 247 mmol) in water (250 ml) was added slowly over a period of 5 minutes and the mixture then stirred at room temperature for 18 hours. The resulting suspension was filtered to give a white solid that was dried in vacuo overnight at 45° C. to yield 45.0 g (88%) of the subtitle compound.

(b) Preparation of N-(2-cyano-1,2,3,4-tetrahydro-5-isoguinolyl)methanesulfonamide

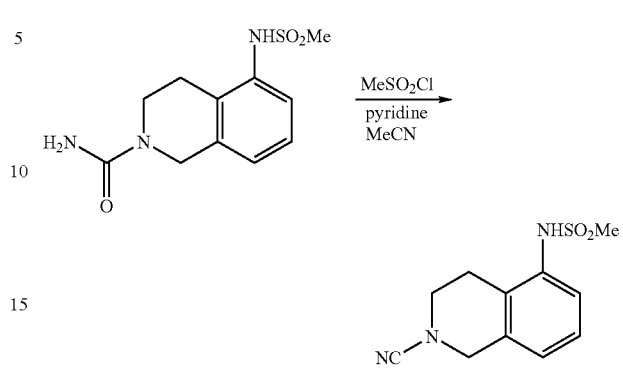

Under nitrogen, N-(2-carboxamide-1,2,3,4-tetrahydro-5-isoquinolyl)methane-sulfonamide [from step (a), 10.0 g, 37.1 mol] was suspended in acetonitrile (100 ml) at 20° C. Methanesulfonyl chloride (6.38 g, 55.6 mmol) and pyridine (7.34 g, 92.8 mmol) were added to the suspension. The reaction was stirred to form a solution then heated to 50° C. and maintained at this temperature for 4 hours. The solution was cooled to room temperature and stirred overnight. The solvent was removed in vacuo and replaced with water (60 ml). The resulting suspension was stirred for 3 hours then filtered to give a white solid. The solid was suspended in acetonitrile (50 ml) and stirred at 20° C. for 3 hours. The suspension was filtered to give a white solid that was dried in vacuo overnight at 45° C. to yield 7.4 g (79%) of the title compound.

EXAMPLE 4

4-amino-2-(5-methanesulfonamido-1,2,3,4-tetrahydro-2-isoquinolyl)-6,7-dimethoxy-5-(2-pyridyl)quinazoline

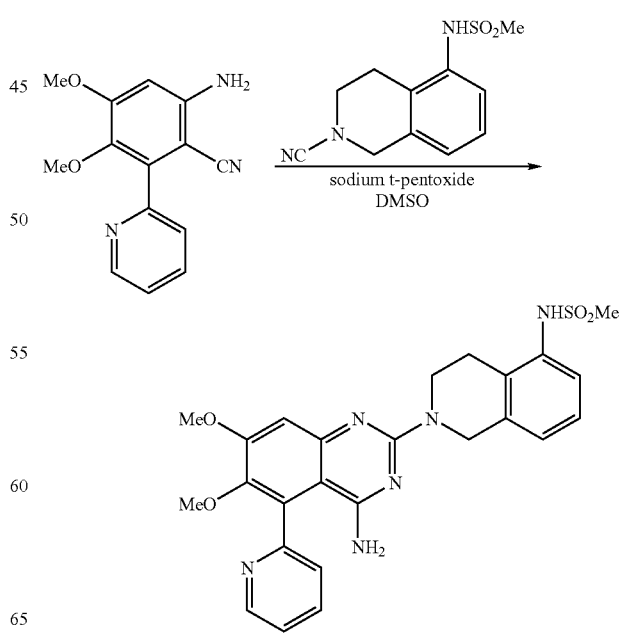

To a stirred solution of 6-amino-3,4-dimethoxy-2-(2-pyridyl)benzonitrile (see Example 2 or 2A, 7 g, 27 mmol) and N-(2-cyano-1,2,3,4-tetrahydro-5-isoquinolyl)methanesulfonamide (see Example 3 or 3A, 9 g, 36 mmol) in DMSO (21 ml) at room temperature, was added sodium-t-pentoxide (9.5 g, 92 mmol) portionwise over 20 minutes keeping the temperature below 30° C. The resulting slurry was then stirred for 2 hours. After this time, iced water (35 ml) was added over 1 minute followed by ethyl acetate (35 ml) before reducing the pH of the biphasic mixture to 8.0 with 2M aqueous HCl (20 ml). The aqueous phase was extracted with ethyl acetate (50 ml). The combined organics were washed with saturated NaCl solution (2×30 ml), reduced in volume and stirred for 3 hours. After this time, the resulting slurry was filtered to yield 10.2 g (74%) of the title compound.

EXAMPLE 4A

Alternative Preparation of 4-amino-2-(5-methanesulfonamido-1,2,3,4-tetrahydro-2-isoquinolyl)-6,7-dimethoxy-5-(2-pyridyl)quinazoline

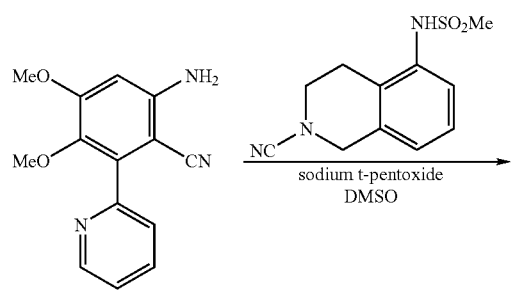

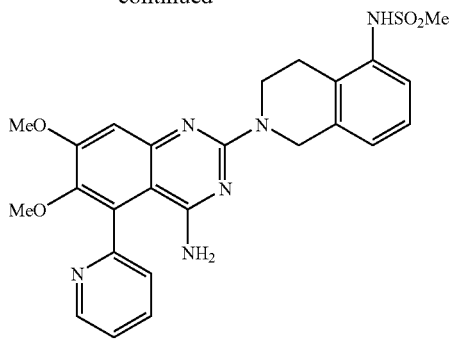

To a stirred solution of 6-amino-3,4-dimethoxy-2-(2-pyridyl)benzonitrile (see Example 2 or 2A, 50 g, 196 mmol) and N-(2-cyano-1,2,3,4-tetrahydro-5-isoquinolyl)methanesulfonamide (see Example 3 or 3A, 63 g, 251 mmol) in DMSO (300 ml) at room temperature, was added sodium-t-pentoxide (64.2 g, 582 mmol) portionwise over 120 minutes keeping the temperature below 30° C. The resulting slurry was then stirred for 2 hours. After this time, water (500 ml) was added over 5 minutes followed by isopropyl acetate (150 ml). The aqueous phase was collected and partitioned with ethyl acetate (500 ml) before reducing the pH of the biphasic mixture to a range of 7.0–8.0 with 12M aqueous HCl (22 ml). The aqueous phase was extracted with ethyl acetate (250 ml). The combined organics were reduced in volume and replaced with acetonitrile to give a final volume of 500 ml and stirred for 13 hours. After this time, the resulting slurry was filtered to yield 105 g of the crude product. This was then suspended in acetonitrile (525 ml), heated to reflux for one hour, cooled to room temperature and stirred for 13 hours. The resulting slurry was filtered to yield 87 g (87%) of the title compound.

The preparation of 4-amino-2-(5-methanesulfonamido-1,2,3,4-tetrahydro-2-isoquinolyl)-6,7-dimethoxy-5-(2-pyridyl)quinazoline according to the above examples is illustrated in the following scheme, which also indicates the Example number of each step and the general formula that covers the relevant compound:

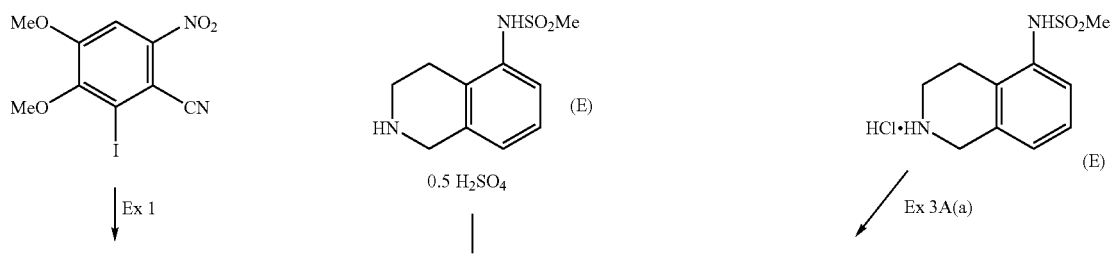

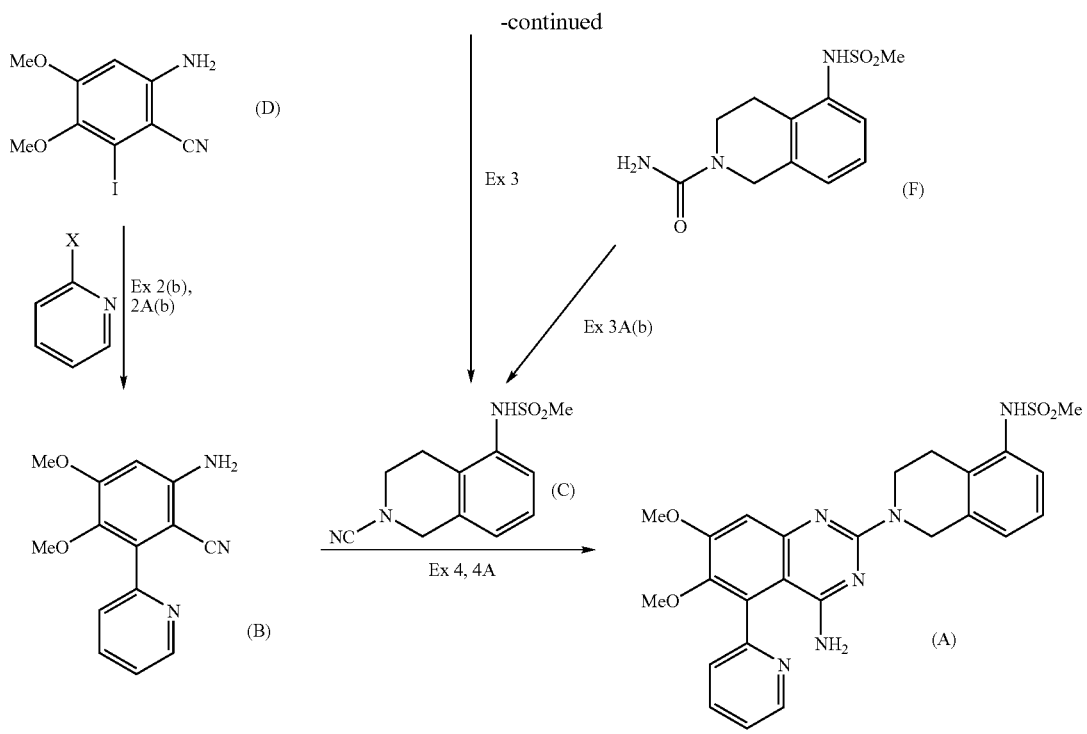

The invention claimed is:
1. A process for the production of a compound of formula (A), or a pharmaceutically acceptable salt or solvate thereof,

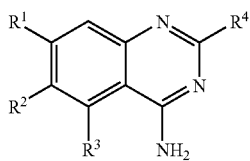
(A)

wherein
R¹ represents $C_{1-4}$ alkoxy optionally substituted by one or more fluorine atoms;
R² represents H or $C_{1-6}$ alkoxy optionally substituted by one or more fluorine atoms;
R³ represents a 5- or 6-membered heterocyclic ring containing at least one heteroatom selected from N, O and S, the ring being optionally substituted by one or more groups selected from halogen, $C_{1-4}$ alkoxy, $C_{1-4}$ alkyl and $CF_3$;
R⁴ is a 4-, 5-, 6- or 7-membered heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^7R^8$, $SO_2NR^7R^8$, $(CH_2)_b NR^7R^8$ and $NHSO_2(C_{1-4}$ alkyl), and when S is a member of the ring system, it may be substituted by 1 or 2 oxygen atoms;
R⁷ and R⁸ independently represent H or $C_{1-4}$ alkyl, or together with the N atom to which they are attached they may represent a 5- or 6-membered heterocyclic ring containing at least one heteroatom selected from N, O and S; and
b represents 0, 1, 2 or 3;
the process comprising condensing a compound of formula (B),

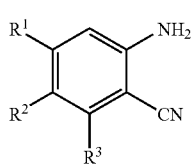
(B)

wherein
R¹ to R³ are as defined above;
with a compound of formula (C),

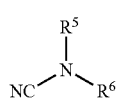
(C)

wherein
R⁵ and R⁶ taken together with the N atom to which they are attached represent a 4-, 5-, 6-, or 7-membered N-containing heterocyclic ring containing at least one heteroatom selected from N, O and S, the ring being optionally fused to a benzene ring or a 5- or 6-membered heterocyclic ring containing at least one heteroatom selected from N, O and S, the ring system as a whole being optionally substituted by one or more groups independently selected from OH, $C_{1-4}$ alkyl, $C_{1-4}$ alkoxy, halogen, $CONR^7R^8$, $SO_2NR^7R^8$, $(CH_2)_bNR^7R^8$ and $NHSO_2(C_{1-4}$ alkyl), and when S is a member of the ring system, it may be substituted by 1 or 2 oxygen atoms;

$R^7$, $R^8$ and b are as defined above; and where necessary or desired, converting the resulting compound of formula (A) into a pharmaceutically acceptable salt or solvate, or converting the resulting salt or solvate into a compound of formula (A).

2. A process as claimed in claim 1, wherein $R^1$ represents methoxy.

3. A process as claimed in claim 1, wherein $R^2$ represents methoxy.

4. A process as claimed in claim 1, wherein $R^3$ represents an aromatic ring.

5. A process as claimed in claim 4, wherein $R^3$ represents 2-pyridyl.

6. A process as claimed in claim 1, wherein $R^5$ and $R^6$ together with the nitrogen to which they are attached, represent a saturated 6-membered N-containing ring which is fused to an optionally substituted benzene or pyridine ring.

7. A process as claimed in claim 6, wherein $R^5$ and $R^6$ together with the nitrogen to which they are attached represent a group of formula

[structure: tetrahydroisoquinoline with NHSO$_2$CH$_3$ substituent]

8. A process as claimed in claim 1, wherein the reaction is carried out in a polar aprotic solvent.

9. A process as claimed in claim 1, wherein the reaction is carried out at a temperature in the range 10–30° C.

10. A process as claimed in claim 1, wherein the reaction is carried out in the presence of a base.

11. A process as claimed in claim 10, wherein the base is an alkali metal alkoxide or an alkaline earth metal alkoxide.

12. A process as claimed in claim 11, wherein the base is sodium t-pentoxide.

13. A process for the production of a compound of formula (C), as defined in claim 1, which comprises reaction of a compound of formula (E), $HNR^5R^6$     (E)

or an acid addition salt thereof, wherein $R^5$ and $R^6$ are as defined in claim 1, with BrCN in the presence of an amine base.

14. A process as claimed in claim 13, wherein the amine is N,N-diisopropylethyl amine.

15. A process for the production of a compound of formula (C), as defined in claim 1, which comprises reaction of a compound of formula (F),

[structure (F): H$_2$N–C(=O)–NR$^5$R$^6$]

wherein $R^5$ and $R^6$ are as defined in claim 1, with methanesulphonyl chloride in the presence of pyridine.

16. A process as claimed in claim 13, wherein the product is N-(2-cyano-1,2,3,4-tetrahydro-5-isoquinolyl)methanesulfonamide.

17. A process for the production of a compound of formula (B),

[structure (B): benzene ring with $R^1$, $R^2$, $R^3$, NH$_2$, CN substituents]

wherein $R^1$ to $R^3$ are as defined in claim 1;

which comprises reaction of a compound of formula (D),

[structure (D): benzene ring with $R^1$, $R^2$, $R^9$, NH$_2$, CN substituents]

wherein;

$R^1$ and $R^3$ are as defined in claim 1;

$R^9$ is a leaving group;

with a pyridyl boronate.

18. A process as claimed in claim 17, wherein $R^9$ is iodine.

19. A process as claimed in claim 17, wherein the pyridine derivative is a 2-pyridyl boronate.

20. A process as claimed in claim 19, wherein the reaction is carried out in a polar aprotic solvent.

21. A process as claimed in claim 20, wherein the polar aprotic solvent is tetrahydrofuran.

22. A process as claimed in claim 21, wherein the reaction is carried out in the presence of a palladium (0) catalyst.

23. A process as claimed in claim 17, wherein the product is 6-amino-3,4-dimethoxy-2-(2-pyridyl)benzonitrile.

24. A compound of formula (B), as defined in claim 1.

25. A compound of formula (C), as defined in claim 1.

26. A process as claimed in claim 1 wherein $R^2$ represents methoxy and $R^3$ represents an aromatic ring.

27. A process as claimed in claim 26 wherein $R^5$ and $R^6$ together with the nitrogen to which they are attached, represent a saturated 6-membered N-containing ring which is fused to an optionally substituted benzene or pyridine ring.

28. A process as claimed in claim 27 wherein $R^3$ represents 2-pyridyl and $R^5$ and $R^6$ together with the nitrogen to which they are attached, represent a group of formula

[structure: tetrahydroisoquinoline with NHSO$_2$CH$_3$ substituent]

29. A process as claimed in claim 28 wherein the reaction is carried out in a polar aprotic solvent at a temperature in the range 10–30° C. and in the presence of a base.

30. A process as claimed in claim 29 wherein the base is an alkali metal alkoxide or alkaline earth metal alkoxide.

31. A process as claimed in claim 22 wherein the product is 6-amino-3,4-dimethoxy-2-(2-pyridyl)benzonitrile.

32. A process as claimed in claim 15 wherein the product is N-(2-cyano-1,2,3,4-tetrahydro-5-isoquinolyl) methanesulfonamide.

* * * * *